US008480707B2

(12) United States Patent
Pavcnik et al.

(10) Patent No.: US 8,480,707 B2
(45) Date of Patent: Jul. 9, 2013

(54) CLOSURE DEVICE AND METHOD FOR OCCLUDING A BODILY PASSAGEWAY

(75) Inventors: Dusan Pavcnik, Portland, OR (US); Kurt J. Tekulve, Ellettsville, IN (US)

(73) Assignees: Cook Medical Technologies LLC, Bloomington, IN (US); Oregon Health and Science University, Portland, OR (US)

( * ) Notice: Subject to any disclaimer, the term of this patent is extended or adjusted under 35 U.S.C. 154(b) by 360 days.

(21) Appl. No.: 12/533,738

(22) Filed: Jul. 31, 2009

(65) Prior Publication Data

US 2010/0030246 A1 Feb. 4, 2010

Related U.S. Application Data

(63) Continuation of application No. PCT/US2008/001376, filed on Feb. 1, 2008.

(60) Provisional application No. 60/898,842, filed on Feb. 1, 2007.

(51) Int. Cl.
*A61B 17/08* (2006.01)

(52) U.S. Cl.
USPC .......................................... 606/213; 606/151

(58) Field of Classification Search
USPC ............... 606/151, 213, 1, 74, 103, 144, 148, 606/157–158, 198, 200, 215, 216, 232; 623/23.72; 24/115 R, 132 R, 135 N, 115 A
See application file for complete search history.

(56) References Cited

U.S. PATENT DOCUMENTS

| 3,012,882 A | 12/1961 | Muldawer et al. |
| 3,174,851 A | 3/1965 | Buechler et al. |
| 3,772,137 A | 11/1973 | Toliver .......................... 161/169 |
| 3,874,388 A | 4/1975 | King et al. .................... 128/334 |
| 4,665,906 A | 5/1987 | Jervis .............................. 128/92 |

(Continued)

FOREIGN PATENT DOCUMENTS

| EP | 1 281 355 A2 | 2/2003 |
| WO | WO 93/10714 | 6/1993 |

(Continued)

OTHER PUBLICATIONS

ISR/Written Opinion of PCT/US2008/001376, dated Aug. 4, 2009, (9p).

(Continued)

*Primary Examiner* — Corrine M McDermott
*Assistant Examiner* — Mark Mashack
(74) *Attorney, Agent, or Firm* — Brinks Hofer Gilson & Lione

(57) ABSTRACT

A device for occluding septal defects or other bodily passageways includes two anchors connected to an occluding body. The occluding body may be formed as a plug or tube of biocompatible material configured to occlude a bodily passageway. At least one of the anchors includes a grasping member in the form of a loop or suitably shaped structure, which is configured for releasable attachment to an anchor engaging member, such as a biopsy forceps. In a further aspect a closure device assembly includes a closure device linked to the biopsy forceps and collapsibly disposed in a catheter. By positioning the catheter near a bodily passageway, such as a PFO, and disengaging the forceps from the grasping member, the closure device may be released so as to facilitate stable closure of a septal opening, such as a PFO.

21 Claims, 7 Drawing Sheets

U.S. PATENT DOCUMENTS

| | | | |
|---|---|---|---|
| 4,675,361 A | 6/1987 | Ward, Jr. | 525/92 |
| 4,917,089 A | 4/1990 | Sideris | 606/215 |
| 5,108,420 A | 4/1992 | Marks | 606/213 |
| 5,334,217 A | 8/1994 | Das | 606/213 |
| 5,595,571 A | 1/1997 | Jaffe et al. | 8/94.11 |
| 5,690,642 A | 11/1997 | Osborne et al. | 606/108 |
| 5,702,421 A | 12/1997 | Schneidt | 606/213 |
| 5,720,777 A | 2/1998 | Jaffe et al. | 623/2 |
| 5,769,796 A | 6/1998 | Palermo et al. | 600/585 |
| 5,814,061 A | 9/1998 | Osborne et al. | 606/194 |
| 5,843,180 A | 12/1998 | Jaffe et al. | 623/2 |
| 5,843,181 A | 12/1998 | Jaffe et al. | 623/2 |
| 5,846,247 A | 12/1998 | Unsworth et al. | 606/108 |
| 5,976,174 A | 11/1999 | Ruiz | 606/213 |
| 5,993,844 A | 11/1999 | Abraham et al. | 424/423 |
| 6,080,182 A | 6/2000 | Shaw et al. | 606/213 |
| 6,113,623 A | 9/2000 | Sgro | 606/215 |
| 6,117,159 A | 9/2000 | Huebsch et al. | 606/213 |
| 6,174,322 B1* | 1/2001 | Schneidt | 606/213 |
| 6,206,907 B1* | 3/2001 | Marino et al. | 606/215 |
| 6,206,931 B1 | 3/2001 | Cook et al. | 623/23.75 |
| 6,264,677 B1* | 7/2001 | Simon et al. | 606/232 |
| 6,358,284 B1 | 3/2002 | Fearnot et al. | 623/23.72 |
| 6,360,577 B2 | 3/2002 | Austin | 72/402 |
| 6,371,961 B1 | 4/2002 | Osborne et al. | 606/108 |
| 6,379,368 B1 | 4/2002 | Corcoran et al. | 606/153 |
| 6,451,052 B1 | 9/2002 | Burmeister et al. | 623/1.16 |
| 6,572,650 B1 | 6/2003 | Abraham et al. | 623/1.38 |
| 6,629,350 B2 | 10/2003 | Motsenbocker | 29/283.5 |
| 6,723,108 B1* | 4/2004 | Jones et al. | 606/151 |
| 6,749,622 B2 | 6/2004 | McGuckin, Jr. et al. | 606/213 |
| 6,783,499 B2 | 8/2004 | Schwartz | 600/486 |
| 6,939,377 B2 | 9/2005 | Jayaraman et al. | 623/1.46 |
| 7,087,072 B2 | 8/2006 | Marino et al. | 606/213 |
| 7,288,105 B2 | 10/2007 | Oman et al. | 606/215 |
| 7,658,751 B2* | 2/2010 | Stone et al. | 606/232 |
| 2001/0010005 A1 | 7/2001 | Kammerer et al. | 606/151 |
| 2001/0034537 A1 | 10/2001 | Shaw et al. | 606/213 |
| 2002/0183787 A1 | 12/2002 | Wahr et al. | 606/213 |
| 2003/0021827 A1 | 1/2003 | Malaviya et al. | 424/423 |
| 2003/0028213 A1 | 2/2003 | Thill et al. | 606/200 |
| 2003/0036801 A1 | 2/2003 | Schwartz et al. | 623/23.63 |
| 2003/0051735 A1 | 3/2003 | Pavcnik et al. | 128/831 |
| 2003/0065361 A1* | 4/2003 | Dreyfuss | 606/232 |
| 2003/0109899 A1 | 6/2003 | Fisher et al. | 606/213 |
| 2003/0114379 A1 | 6/2003 | Li et al. | 514/12 |
| 2003/0144695 A1 | 7/2003 | McGuckin, Jr. et al. | 606/213 |
| 2003/0191495 A1 | 10/2003 | Ryan et al. | 606/213 |
| 2003/0206860 A1 | 11/2003 | Bleyer et al. | 424/9.4 |
| 2003/0225421 A1 | 12/2003 | Peavey et al. | 606/151 |
| 2004/0049211 A1 | 3/2004 | Tremulis et al. | 606/153 |
| 2004/0073242 A1 | 4/2004 | Chanduszko | 606/157 |
| 2004/0078053 A1 | 4/2004 | Berg et al. | 606/213 |
| 2004/0093017 A1 | 5/2004 | Chanduszko | 606/200 |
| 2004/0098042 A1* | 5/2004 | Devellian et al. | 606/213 |
| 2004/0133236 A1 | 7/2004 | Chanduszko | 606/213 |
| 2004/0143277 A1 | 7/2004 | Marino et al. | 606/157 |
| 2004/0143293 A1 | 7/2004 | Marino et al. | 606/213 |
| 2004/0143294 A1 | 7/2004 | Corcoran | 606/213 |
| 2004/0166169 A1 | 8/2004 | Malaviya et al. | 424/551 |
| 2004/0176799 A1 | 9/2004 | Chanduszko et al. | 606/213 |
| 2004/0213756 A1 | 10/2004 | Michal et al. | 424/78.17 |
| 2004/0220596 A1 | 11/2004 | Frazier et al. | 606/153 |
| 2004/0230222 A1 | 11/2004 | van der Burg et al. | 606/215 |
| 2004/0249398 A1 | 12/2004 | Ginn | 606/151 |
| 2004/0267306 A1 | 12/2004 | Blaeser et al. | 606/213 |
| 2005/0043759 A1 | 2/2005 | Chanduszko | 606/213 |
| 2005/0065547 A1 | 3/2005 | Marino et al. | 606/213 |
| 2005/0070794 A1 | 3/2005 | Deal et al. | 600/434 |
| 2005/0070821 A1 | 3/2005 | Deal et al. | 600/585 |
| 2005/0085885 A1 | 4/2005 | Janke et al. | 607/122 |
| 2005/0090859 A1 | 4/2005 | Ravlkumar | 606/213 |
| 2005/0125050 A1 | 6/2005 | Carter et al. | 623/1.11 |
| 2005/0155608 A1 | 7/2005 | Pavcnik et al. | 128/831 |
| 2005/0192626 A1 | 9/2005 | Widomski et al. | 606/213 |
| 2005/0234509 A1 | 10/2005 | Widomski et al. | 606/213 |
| 2005/0249772 A1 | 11/2005 | Malaviya et al. | 424/423 |
| 2005/0251154 A1 | 11/2005 | Chanduszko et al. | 606/151 |
| 2005/0267524 A1 | 12/2005 | Chanduszko | 606/213 |
| 2005/0273119 A1 | 12/2005 | Widomski et al. | 606/151 |
| 2005/0273124 A1 | 12/2005 | Chanduszko | 606/159 |
| 2005/0273135 A1* | 12/2005 | Chanduszko et al. | 606/213 |
| 2005/0288682 A1* | 12/2005 | Howe | 606/104 |
| 2005/0288706 A1 | 12/2005 | Widomski et al. | 606/213 |
| 2006/0008419 A1 | 1/2006 | Hissink et al. | 424/45 |
| 2006/0052816 A1 | 3/2006 | Bates et al. | 606/200 |
| 2006/0122647 A1 | 6/2006 | Callaghan et al. | 606/213 |
| 2006/0200196 A1 | 9/2006 | Zang et al. | 606/213 |
| 2006/0201996 A1 | 9/2006 | Hodde | 228/101 |
| 2006/0217760 A1 | 9/2006 | Widomski et al. | 606/213 |
| 2006/0217761 A1 | 9/2006 | Opolski | 606/213 |
| 2006/0241687 A1* | 10/2006 | Glaser et al. | 606/213 |
| 2008/0091235 A1 | 4/2008 | Sirota | 606/215 |

FOREIGN PATENT DOCUMENTS

| | | |
|---|---|---|
| WO | WO 2005/027752 A1 | 3/2005 |
| WO | WO 2006/110147 A2 | 10/2006 |
| WO | WO 2006/119256 A2 | 11/2006 |
| WO | WO 2007/092274 A1 | 8/2007 |
| WO | WO 2008/094706 A2 | 8/2008 |

OTHER PUBLICATIONS

Braun, M., et al., "*Transcatheter Closure of Patent Foramen Ovale (PFO) in Patients With Paradoxical Embolism*", European Heart Journal (2004), vol. 25, pp. 424-430.

Das, Gladwin S., et al., "*Experimental Atrial Septal Defect Closure With a New, Transcatheter, Self-Centering Device*", Circulation, vol. 88, No. 4, Part 1, Oct. 1993, pp. 1754-1764.

Heeschen, Christopher, et al., "*Nicotine Stimulates Angiogenesis and Promotes Tumor Growth and Atherosclerosis*", Nature Medicine vol. 7, No. 7, (Jul. 2001), pp. 833-839.

Johnson, Chad, et al., "*Matrix Metalloproteinase-9 is Required for Adequate Angiogenic Revascularization of Ischemic Tissues*", Circulation Research, Feb. 6, 2004, No. 94, pp. 262-268.

Jux, Christian, et al., "*A New Biological Matrix for Septal Occlusion*", Journal of Interventional Cardiology, vol. 16, No. 2, (2003), pp. 149-152.

Jux, Christian, et al., "*Interventional Atrial Septal Defect Closure Using a Totally Bioresorbable Occluder Matrix*", JACC, vol. 48, No. 1, (2006), pp. 161-169.

King, Terry D., et al., "*Secundum Atrial Septal Defect—Nonoperative Closure During Cardiac Catheterization*", JAMA, vol. 235, No. 23, Jun. 7, 1978, pp. 2506-2509.

Mullen, Michael J., et al., "*BioSTAR Evaluation STudy (BEST) A Prospective, Multicenter, Phase I Clinical Trial to Evaluate the Feasibility, Efficacy, and Safety of the BioSTAR Bioabsorbable Septal Repair Implant for the Closure of Atrial-Level Shunts*", Circulation, Oct. 31, 2006, pp. 1962-1967.

Pavcnik, Dusan et al., "*Monodisk: Device for Percutaneous Transcatheter Closure of Cardiac Septal Defects*", Cardiovasc Intervent Radiol (1993) vol. 16, pp. 308-312.

Rashkind, William J., "*Transcatheter Treatment of Congenital Heart Disease*", Circulation vol. 67, No. 4, Apr. 1983, pp. 711-716.

Sideris, E.B. et al., "*Transvenous Atrial Septal Defect Occlusion in Piglets with a "Buttoned" Double-Disk Device*", Circulation, vol. 81, No. 1, Jan. 1990, pp. 312-318.

*Transcatheter Closure of Atrial Septal Defects*, The Lancet, Sep. 1, 1990, pp. 566-567.

\* cited by examiner

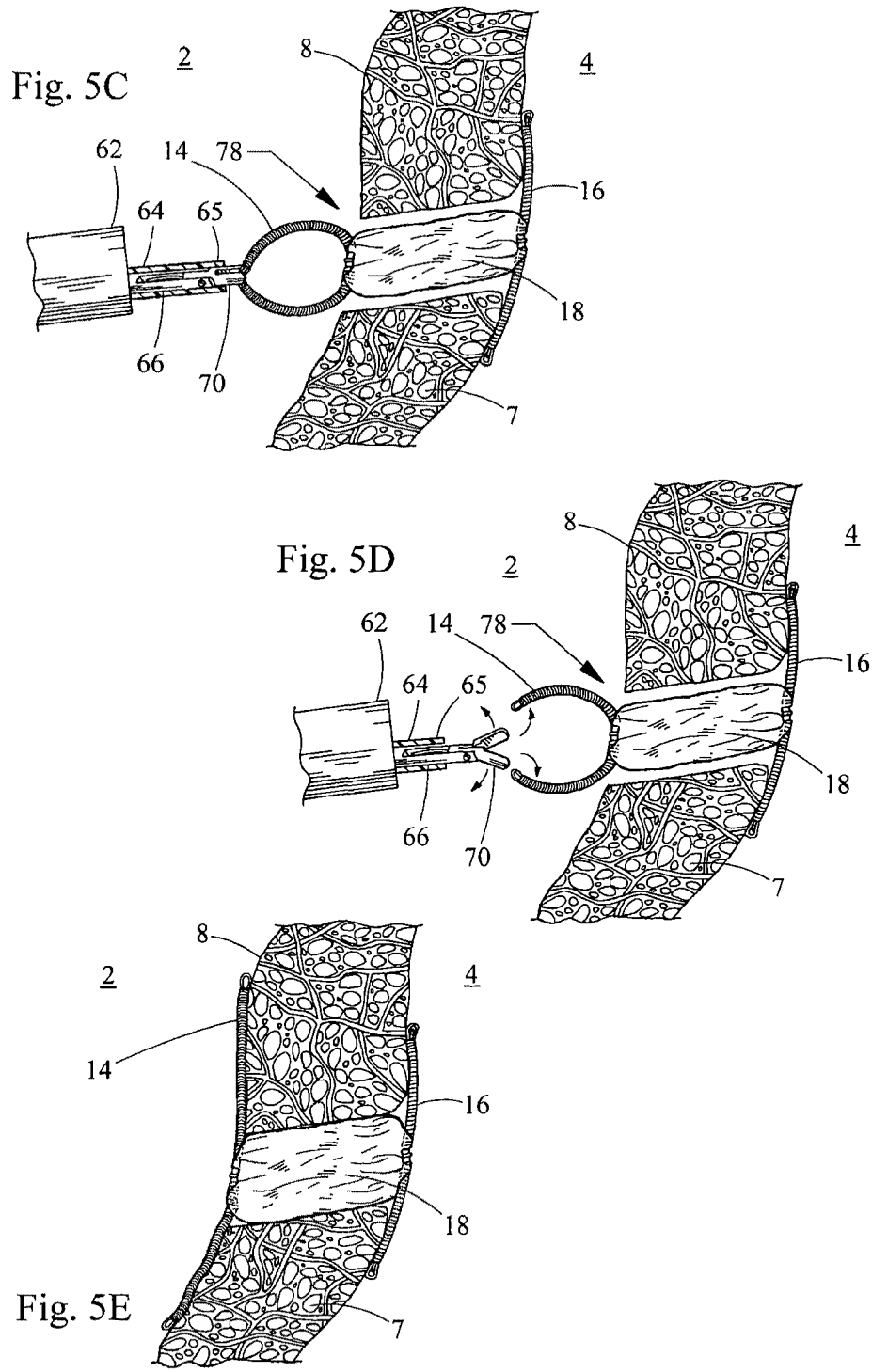

CLOSURE DEVICE AND METHOD FOR OCCLUDING A BODILY PASSAGEWAY

The present application is a continuation of PCT International Application Serial Number PCT/US2008/001376, filed Feb. 1, 2008, which designates the U.S. and was published in English, and which claims priority to U.S. Provisional Patent Application Ser. No. 60/898,842, filed Feb. 1, 2007, both of which are hereby incorporated by reference.

BACKGROUND

This application relates to the closure of a bodily passage such as a septal opening and such as a patent foramen ovale.

A patent foramen ovale (PFO) is a persistent, one-way, usually flap-like opening in the wall between the right atrium and left atrium of the heart. In utero, the foramen ovale serves as a physiologic conduit for right-to-left shunting of blood in the fetal heart. Because blood is oxygenated through the umbilical chord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure presses the septum primum against the walls of the septum secundum, covering the foramen ovale and resulting in functional closure of the foramen ovale. This closure is usually followed by anatomical closure of the foramen ovale due to fusion of the septum primum to the septum secundum.

Where anatomical closure of the foramen ovale does not occur, a PFO is created. Studies have shown that a relatively large percentage of adults have a PFO The presence of a PFO is generally considered to have no therapeutic consequence in otherwise healthy adults. Because left atrial (LA) pressure is normally higher than right atrial (RA) pressure, the flap usually stays closed. Under certain conditions, however, right atrial pressure can exceed left atrial pressure, creating the possibility that blood could pass from the right atrium to the left atrium and blood clots could enter the systemic circulation. It is desirable that this circumstance be eliminated.

Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. It has been estimated that in 50% of cryptogenic strokes, a PFO is present. In addition, there is significant evidence that patients with a PFO who have had a cerebral vascular event are at increased risk for future, recurrent cerebrovascular events.

Patients suffering a cryptogenic stroke or a transient ischemic attack (TIA) in the presence of a PFO often are considered for medical therapy to reduce the risk of a recurrent embolic event. Accordingly, patients at such an increased risk are considered for prophylactic medical therapy to reduce the risk of a recurrent embolic event. These patients are commonly treated with oral anticoagulants to reduce the risk of a recurrent embolic event. However, these anticoagulants have potentially adverse side effects, including hemorrhaging, hematoma, and adverse interactions with other drugs. In addition, use of anticoagulant drugs can alter a person's recovery and necessitate adjustments in a person's daily living pattern.

Where anticoagulation is contraindicated, surgery may be employed to close a PFO. The surgery would typically include suturing a PFO closed by attaching septum secundum to septum primum. Like other open surgical treatments, however, this surgery is highly invasive, risky, requires general anesthesia, and may result in lengthy recuperation.

Nonsurgical closure of PFOs has become possible with the introduction various mechanical closure devices, including umbrella devices and the like, which were initially for percutaneous closure of atrial septal defects (ASDs; a condition where there is not a septum primum). These devices potentially allow patients to avoid the side effects often associated with anticoagulation therapies and the risks of invasive surgery.

However, devices for treating heart defects, such as PFO and other atrial and ventricular septal heart defects have their share of drawbacks. The complex anatomical features of PFOs present a challenge to a one size fits all approach. The PFO involves two components, septum primum and septum secundum. The septum secundum is thicker than septum primum and exhibits limited mobility and compliance. Failure of these two structures to fuse creates a tunnel-like passageway, the PFO. The distance of the nonfusion between the two septa determines the particular size of the PFO, which must be considered in the design of a device targeting PFOs. Nevertheless, devices are often configured so that the patient's anatomy must be adjusted to fit the geometry of the device. As a consequence, heart tissue may be torn when accommodating such devices.

Conventional nonsurgical closure devices are often technically complex, bulky, have a high septal profile, low radiopacity, and an inability to provide immediate closure. Additionally, many of the devices have a geometry which tends to prevent the device from remaining flat against, or within the defect once deployed. The varying passageway geometries often require multiple sized devices. Moreover, many devices are set apart by a relatively long central section corresponding to the PFO tunnel. By increasing the device profile, the device can present difficulties with respect to complete endothelialization. Conventional closure devices are often difficult to deploy or reposition, often require replacement or repositioning, and require relatively large delivery catheters (for example, 9-10 French or more). In addition, the large masses of foreign material associated with the device may lead to unfavorable body adaptation to the device, including thromboses or other unfavorable reactions. Further drawbacks to nonsurgical closure devices include complications resulting from fractures of the components, conduction system disturbances, perforations of heart tissue, residual leaks, and inability to allow subsequent methods involving transeptal puncturing.

Accordingly, there is a need for improved low profile closure devices and simplified delivery methods for improved closure, which are capable of limiting the amount of foreign material deployed and enhancing closure stability. The present invention is designed to address a number of the deficiencies surrounding conventional closure devices.

SUMMARY

A device for occluding a bodily passageway, such as a septal defect, includes an occluding body positioned between proximal and distal anchors. The occluding body may include a plug or tube of bioremodelable material configured to occlude a bodily passageway. Each of the proximal and distal anchors may comprise a flexible structure and at least one anchor comprises a grasping member. The grasping member is configured for releasable attachment to an anchor engaging member facilitating delivery of the device.

The proximal and distal anchors are configured to stably localize the occluding body within the bodily passageway. In particular, the proximal and distal anchors are preferably configured to contact distal and proximal sides of a septum and hold the occluding body in an opening within the septum. In a particular embodiment, each of the proximal and distal anchors is formed as a substantially one-dimensional linear structure that can rotate relative to the longitudinal axis of the plug or tube when deployed.

Each anchor may be formed as a coiled structure having at least one anchor coil, whereby at least one the coiled structures includes a proximally positioned grasping member configured for releasable attachment to an anchor engaging member facilitating delivery of the device. Preferably, the grasping member includes a loop structure. Suitable anchor engaging members, including biopsy forceps, may be disposed within a delivery catheter and linked to the closure device via one or more grasping member(s) to facilitate positioning and release of the anchors from the delivery catheter, as well as uncoupling of the closure device from the delivery catheter in connection with its deployment. In a preferred embodiment, each anchor includes an anchor coil and an anchor wire longitudinally extending through the anchor coil, whereby the anchor wire includes at least one terminally disposed grasping member or loop structure frictionally engaged by the anchor coil.

The two anchors are connected to the occluding body by one or more linking members. Suitable linking members include sutures, coils, wires, clips, staples, adhesives, combinations thereof, or any other suitable attachment materials or attachment structures known to those of skill in the art.

In one embodiment, the linking member extends through a hole in the occluding body. In this case, the linking member may include one or more sutures connectively linking the occluding body to the anchors. In a particularly preferred embodiment, the linking member includes an occluding body coil and one or more wire(s) longitudinally extending therethrough, the occluding body coil and wire(s) connectively linking the anchors to the occluding body.

One or more component parts of the closure device may be made from shape memory alloy materials, such as Nitinol, and may include radiopaque materials to facilitate visualization of the device during deployment. The occluding body, including the plug or tube, includes one or more collagenous extracellular matrix materials. In a particular aspect, the plug or tube is formed from an expandable submucosal matrix material.

In a further aspect, an assembly and method for delivering the closure device includes a delivery catheter containing the above described closure device collapsibly disposed therein. A terminally disposed grasping member is attached to an anchor engaging member, such as a biopsy forceps. The anchor engaging member may be advanced to release the closure device from its collapsed state near a site proximal to a septal defect, such as a PFO. Upon disengagement of the grasping member from the anchor engaging member, the plug or tube of bioremodelable material occludes at least a portion of the bodily passageway and is secured therein by the anchors. In a preferred embodiment, the method is used to close a PFO.

BRIEF DESCRIPTION OF THE DRAWINGS

FIG. 5C shows a cross-sectional view of the distal end of the closure device assembly of FIG. 4B showing attachment of the proximal anchor to the biopsy forceps and positioning of the proximal anchor on the proximal side of the PFO opening.
FIG. 5D shows a cross-sectional view of the distal end of the closure device assembly of FIG. 4B showing retraction of the locking catheter sheath and disengagement of the proximal anchor from the biopsy forceps
FIG. 5E shows a cross-sectional view illustrating a deployed closure device closing a PFO.

DETAILED DESCRIPTION

Figure 1:
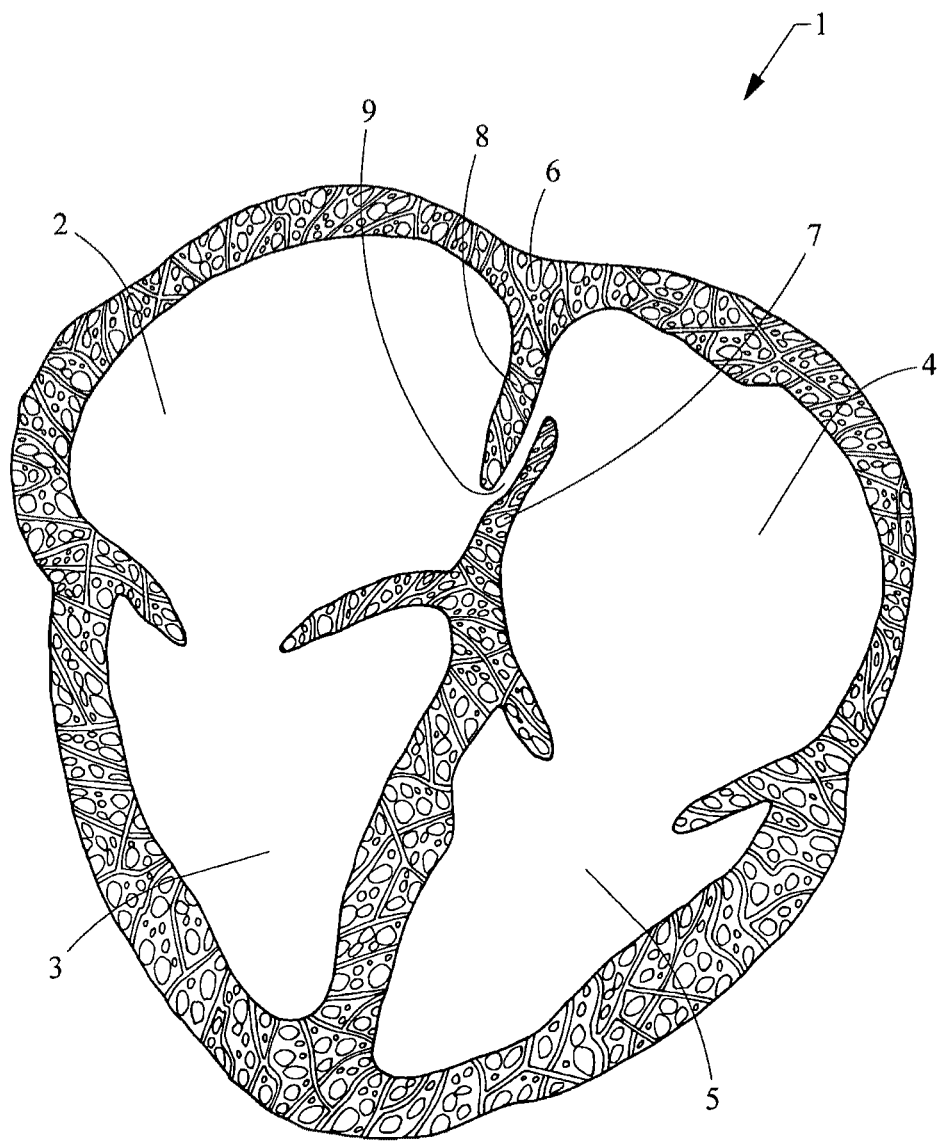
FIG. 1 shows a cross-sectional view of a heart with a PFO.

A closure device for closing or occluding bodily passageways, including septal openings of the heart is provided. Without wishing to be bound by a particular theory or to in any way limit the scope of the appended claims and their equivalents, it is believed that incorporation of (preferably expandable) bioremodelable material capable of causing angiogenesis and replacement by host tissues according to aspects of the present invention provides a more stable and permanent closure relative to conventional closure devices.

In order to provide a clear and consistent understanding of the specification and claims, the following definitions are provided.

As used herein, the terms "opening", "bodily opening", "passageway", and "bodily passageway" are interchangeably used to refer to a bodily opening, aperture, canal, conduit, or duct, including but not limited to septal openings, heart valves, blood vessels, vessel punctures, bile ducts, and the like.

The terms "connected", "connecting", "connectively linked" and "connectively linking" interchangeably refer to the joining, adhering, bonding, attaching, or the like, of two elements. Two elements will be considered to be connected together when they are connected directly to one another or indirectly to one another, such as when each is directly connected to intermediate elements.

The term "anchor" refers to a flexible, preferably substantially linear structure in a closure device of the present invention which is configured to be positioned on either side of a bodily passageway so as to anchor an occluding body in the bodily passageway.

The term "grasping member" refers to a grasping structure on an anchor having a shape suitable (for example, loop, knob, ball, hook, and the like) for releasable attachment to an anchor engaging member. The grasping member may be integral to a tube, coil or bar in an anchor or it may be disposed on a second structure separate from and connected to the tube, coil or bar.

The term "anchor engaging member" refers to a member facilitating delivery of the closure device by releasable attachment to at least one anchor by way of one or more grasping members.

The term "anchor engagement portion" refers to a portion of the anchor engaging member having a complementary structure configured for linkage and releasable attachment to the grasping member.

As used herein, the term "biocompatible" refers to a material that is substantially non-toxic in the in vivo environment of its intended use, and that is not substantially rejected by the patient's physiological system or is non-antigenic. This can be gauged by the ability of a material to pass the biocompatibility tests set forth in International Standards Organization (ISO) Standard No. 10993; the U.S. Pharmacopeia (USP) 23; or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, immunogenicity, and combinations thereof. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

As used herein, the term "bioresorbable" refers to refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", and "bioabsorbable" are frequently used interchangeably.

As used herein, the term "bioremodelable" refers to a natural or synthetic material that is bioresorbable and capable of inducing angiogenesis, tissue remodeling, or both in a subject or host. A bioremodelable material includes at least one bioactive agent capable of inducing angiogenesis or tissue remodeling. The bioactive agent(s) in the bioremodelable material may stimulate infiltration of native cells into an acellular matrix, and formation of new blood vessels (capillaries) growing into the matrix to nourish the infiltrating cells (angiogenesis). Additionally, the bioactive agent(s) may effect the degradation or replacement of the bioremodelable material by endogenous tissue. The bioremodelable material may include a naturally derived collagenous extracellular matrix (ECM) structure present in, for example, native submucosal tissue sources, including, but not limited to small intestine submucosal (SIS) tissue, or it may include any one of a variety of different non-submucosal ECM-containing tissue materials or synthetic, bioresorbable non-ECM materials capable of inducing angiogenesis and tissue remodeling in a host.

The terms "angiogenesis and angiogenic" refer to bioremodelable properties defined by formation of capillaries or microvessels from existing vasculature in a process necessary for tissue growth, where the microvessels provide transport of oxygen and nutrients to the developing tissues and remove waste products.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers, such the lamina muscularis mucosa and the stratum compactum. A submucosal material may be a decellularized or acellular tissue, which means it is devoid of intact viable cells, although some cell components may remain in the tissue following purification from a natural source. Alternative embodiments (for example, fluidized compositions and the like) include submucosal material expressly derived from a purified submucosal matrix structure. Submucosal materials according to the present disclosure are distinguished from collagen materials in other closure devices that do not retain their native submucosal structures or that were not prepared from purified submucosal starting materials first removed from a natural submucosal tissue source.

The term "small intestinal submucosa" (SIS) refers to a particular submucosal tissue structure removed from a small intestine source, such as pig.

The term "radiopaque" refers to a non-toxic material capable of being monitored or detected during injection into a mammalian subject by, for example, radiography or fluoroscopy. The radiopaque material may be either water soluble or water insoluble. Examples of water soluble radiopaque materials include metrizamide, iopamidol, iothalamate sodium, iodomide sodium, and meglumine. Examples of water insoluble radiopaque materials include tantalum, tantalum oxide, and barium sulfate, which are commercially available in the proper form for in vivo use. Other water insoluble radiopaque materials include, but are not limited to, gold, tungsten, stainless steel, and platinum.

FIG. 1 is a schematic front view of a heart 2 with a septal defect, such as patent foramen ovale (PFO). The heart 1 has a right atrium 2, right ventricle 3, left atrium 4, and a left ventricle 5. The septum 6 between the right atrium 2 and the left atrium 4 comprises a septum primum 7 and a septum secundum 8. The PFO 9 is a passageway in the septum 6 that has not properly closed. Where a PFO 9 is present, the septum primum 7 typically overlaps the septum secundum 8 and the higher pressure in the left atrium 4 typically closes the flaps of the septum primum 7 and the septum secundum 8 so that blood does not leak between the atria 2 and 4. However, when there is a pressure change in the chest, the flaps may separate permitting blood to flow through the PFO and between the atria 2 and 4.

In one aspect of the present invention, a closure device for occluding a bodily passageway includes an occluding body connected between proximal and distal anchors. The anchors are connected to the occluding body by one or more linking members. The occluding body is formed as a plug or tube of biocompatible material or bioremodelable material, which is configured to close, occlude, or fill at least a lumenal portion of a bodily passageway. Exemplary biocompatible and bioremodelable materials are described below.

The anchors may be configured to include at least one tube, coil, or bar. The tube or bar may be hollow or substantially filled. Hollow anchor portions may be filled with or include other material elements, such as wires. In one embodiment, one or both of the anchors includes a flexible, substantially one-dimensional linear structure having a first end and second end. Preferably, the anchors can rotate relative to the longitudinal axis of the plug or tube when deployed. The proximal anchor includes at least one grasping member having a structure suitable for releasable attachment to an anchor engaging member facilitating delivery of the closure device.

One or both anchors may include a coil and a grasping member formed from a wire extending through the coil. The grasping member may include a loop structure or other suitable structure configured for releasable attachment to an anchor engaging member facilitating delivery of the closure device.

Figure 2A:
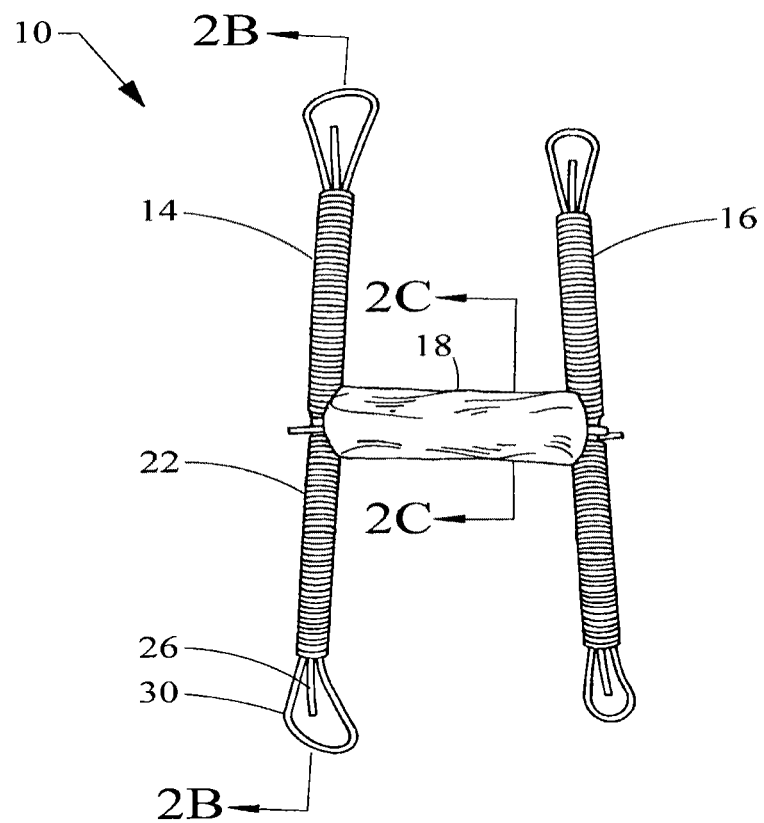
FIG. 2A shows a plan view of an exemplary closure device according to an embodiment of the present invention.

FIG. 2A shows an exemplary closure device 10 according to an embodiment of the present invention. The closure device 10 includes proximal and distal anchors 14, 16 linked to an occluding body 18. In FIG. 2A, the proximal anchor 14 and the distal anchor 16 each include an anchor coil 22 with one or more anchor wires 26 extending longitudinally therethrough.

Each of the anchors 14, 16 in FIG. 2A includes two terminally disposed grasping members 30 formed from an anchor wire 26 extending through the anchor coil 22 in the shape of a loop. However, grasping members 30 can be configured to include virtually any graspable structure or shape suitable (for example, knob or ball) for releasable attachment to an anchor engaging member facilitating delivery of the closure device 10. A closure device 10 of the present invention must contain at least one grasping member 30; the grasping member(s) 30 may be connected to the proximal anchor 14 only or to both the proximal anchor 14 and the distal anchor 16. The grasping member(s) 30 may be connected to any anchor region suitable for releasable attachment to an anchor engaging member facilitating delivery of the closure device 10. Preferably, the grasping member(s) 30 are disposed at the terminal ends of one or both of the anchors 14, 16. The grasping member(s) may be connected to the anchor or they may be integral to any anchor component. More preferably, the grasping members(s) 30 include terminally disposed loop structures.

Suitable anchor engaging members may include a biopsy forceps, ball, hook, loop, pair of cups or jaws, or any other suitable member capable of releasable attachment to a grasping member.

Figure 2C:
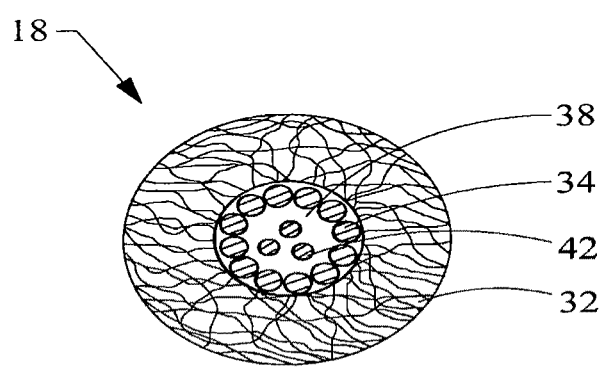
FIG. 2C shows a cross-sectional view of an exemplary closure device according to an embodiment of the invention.
Figure 2B:
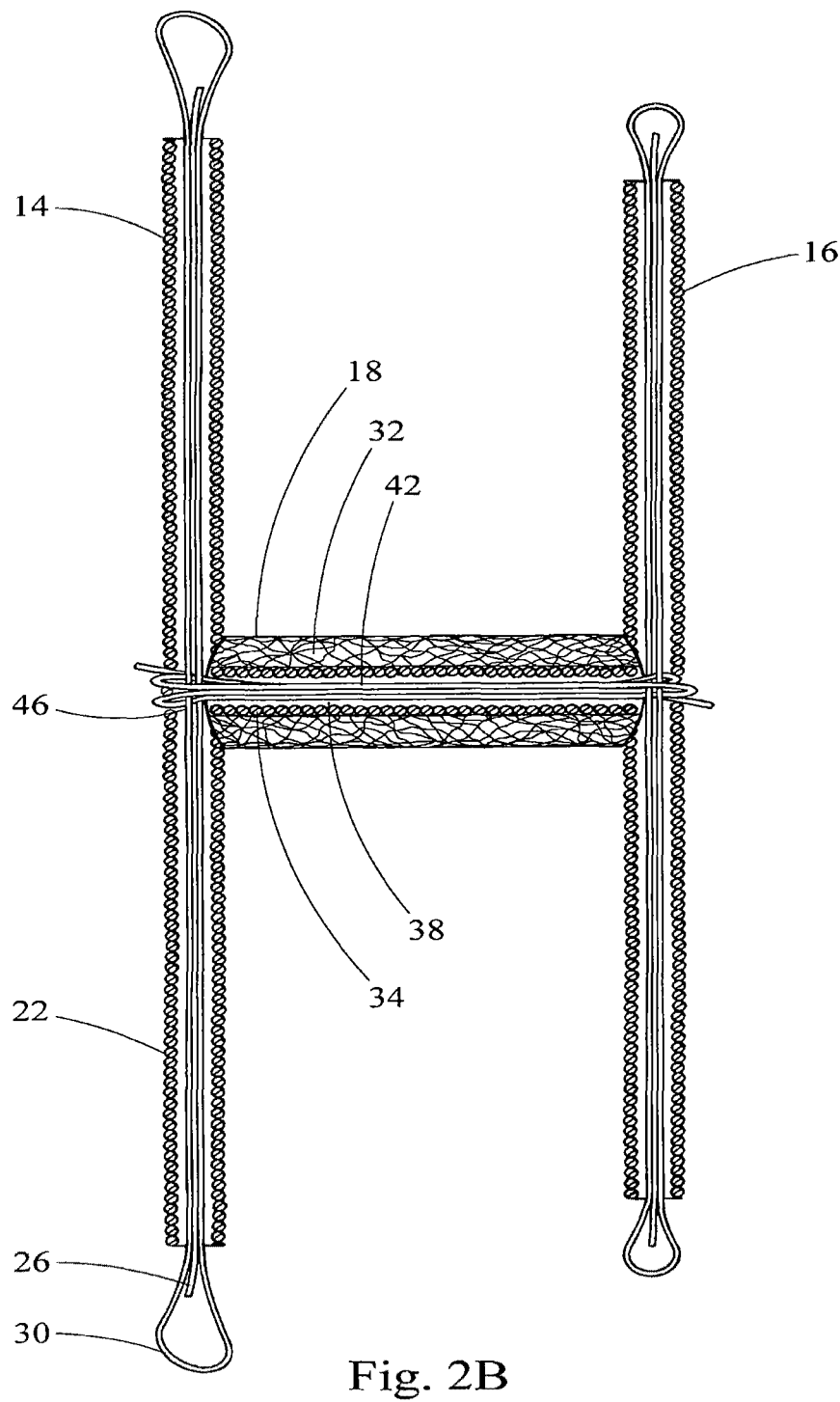
FIG. 2B shows a side view of an exemplary closure device according to an embodiment of the present invention.

The proximal and distal anchors 14, 16 are connected to the occluding body 18 by one or more linking members. Suitable linking members include one or more sutures, wires, coils, clips, staples, adhesives or other suitable linking materials known to those of skill in the art. FIGS. 2A-2C depict an occluding body 18 with an occluding body coil 34 and occluding body wires 42 extending therethrough.

FIG. 2B depicts a longitudinal cross-sectional view of the closure device of FIG. 2A taken along line 2B-2B illustrating exemplary linking members according to the present invention. FIG. 2C depicts a cross-sectional view of the occluding body 18 of FIG. 2B taken along line 2C-2C. In FIGS. 2B and 2C, the occluding body 18 includes a hollow occluding body tube 32 and an occluding body coil 34 extending through a hollow, lumenal portion 38 of the occluding body 18. Occluding body wires 42 extending therethrough, connectively linking the anchors 14, 16 to the occluding body 18. Although FIGS. 2A-2C depict an occluding body 18 having an occluding body coil 34 and occluding body wires 42 extending therethrough, the occluding body 18 may be formulated without an occluding body coil 34 or without occluding body wires 42. For example, sutures may substitute for the occluding body coil 34, the occluding body wires 42, or both, in connectively linking the occluding body 18 to the anchors 14, 16. Alternatively, sutures may be used in addition to, or as an alternative to either one of the occluding body coil 34 and occluding body wires 42 for securing the anchors 14, 16 to the occluding body 18.

Linking members may extend through one or more portions of the occluding body 18. FIGS. 2A-2C depict linking members extending through the hollow tube 32 of the occluding body 18. Alternatively, the linking members may be threaded through one or more holes disposed in the occluding body 14, including a hole longitudinally disposed therethrough.

FIG. 2B illustrate anchor coil center portions 46 interrupted by small gaps in each of the two anchors 14, 16. By partially stretching the anchor coil center portion 46 in each anchor coil 22, small gapped areas are created, which serve to enhance the ability of the occluding body wires 42 to wrap around and securely engage the two anchors 14, 16. Sutures may be used instead of or in addition to the occluding body wires 42. In the resulting connection, the occluding body 18 may be directly abutted against both anchors 14, 16. Alternatively, the occluding body 18 in the closure device 10 may be configured to overlap or partially overlap with the anchor(s) 14, 16.

In one aspect, the occluding body 18 includes a plug or hollow tube 32 of bioremodelable material, preferably submucosal material, which is configured to substantially fill a lumenal portion of the bodily passageway. The occluding body 18 may be variably sized depending on the lumenal size of the bodily passageway for occlusion. To facilitate occlusion, the occluding body 18 may be formulated with a material capable of radially expanding when hydrated.

In one embodiment, the occluding body 18 is formed as a hollow tube 32 of compressed, lyophilized biocompatible material. Preferably the tube 32 of biocompatible material includes or is made from collagenous extracellular matrix material. In a particularly preferred embodiment, the occluding body 18 includes a compressed, lyophilized tube 32 of expandable submucosal material, particularly small intestinal submucosal (SIS) material.

The compressed tube 32 of submucosal material may be made by rolling a hydrated sheet of submucosal material (such as SIS) into the form of a hollow tube 32. The tube 32 is lyophilized and an occluding body coil 34 is longitudinally extended through the hollow lumenal portion 38. An occluding body coil 34 may be inserted through the lyophilized tube 32 to add support and to facilitate passage of wires, sutures, guide wires, and the like. After sliding the occluding body coil 34 into the hollow occluding body tube 32, the submucosal material may be compressed onto the occluding body coil 34 using a suitable stent crimping/compressing apparatus (Machine Solutions, Inc., Flagstaff, Ariz.) as described in, for example, U.S. Pat. Nos. 6,629,350, and 6,360,577, the disclosures of which are incorporated by reference herein. An iris-type stent compressing apparatus is an exemplary apparatus, which includes a plurality of blades which are disposed about an opening and which can open and close in an iris-like manner. Other compression devices that may also be used in the practice of the invention are known to those of skill in the art.

Exemplary bioremodelable plug or tube embodiments, including those made from ECMs and synthetic polymers, are disclosed in U.S. Patent Application Publication Nos. 2006/0052816, 2005/0155608, 2005/0249772, 2004/0166169, 2003/0051735, and 2003/0036801; U.S. Provisional Patent Application No. 60/676,118, filed Apr. 29, 2005; and PCT/US2006/016748, filed Apr. 29, 2006, the disclosures of which are expressly incorporated by reference herein.

The length of the plug or compressed tube 32 may be modified depending on the length of the bodily passageway for occlusion. For use in occluding PFO tunnels, the plug or tube 32 of biocompatible material is preferably between about 2 mm and about 12 mm in length.

The outer diameter of the occluding body 18 is sufficiently formulated to substantially fill a lumenal portion of the bodily passageway. By way of example, when occluding a PFO, the plug or compressed tube 32 of biocompatible or bioremodelable material, such as submucosal material, may be formulated to have a lyophilized (or compressed) outer diameter between about 1 mm and about 3 mm, and a hydrated (expanded) outer diameter of about 8 mm and about 20 mm. Of course, the diameter can be modified depending on the nature and expandability of the biocompatible or bioremodelable materials and the diameter of the bodily passageway for occlusion.

The inner diameter of the hollow tube 32 of biocompatible or bioremodelable material may be varied depending on the manner and spatial requirements for linking the proximal 14 and distal anchor 16 to the occluding body 18. In a particular aspect, the hollow occluding body tube 32 may be formulated with a sufficiently large inner diameter to allow wire guide access through the tube 32 for over-the-wire (OTW) or rapid exchange delivery procedures known to those of skill in the art.

The anchors 14, 16 may be variably sized depending on the size of the bodily passageway or septal opening, such as a PFO. Generally, the anchors 14, 16 are configured to overlap the opening at either end of the bodily passageway and to become stably secured thereto. Thus, the anchors 14, 16 are configured to sandwich the occluding body 18 into the bodily passageway. The length of the anchors 14, 16 can be modified depending on the size of the opening. For example, the anchor may have a length between about 5 to about 50 mm, preferably between about 10 to about 30 mm, still more preferably between about 15 to about 25 mm. The proximal 14 and distal 16 anchors may be configured with the same or different lengths. As shown in FIG. 2A, the proximal anchor 14 may be longer than the distal anchor 16.

Figure 3:
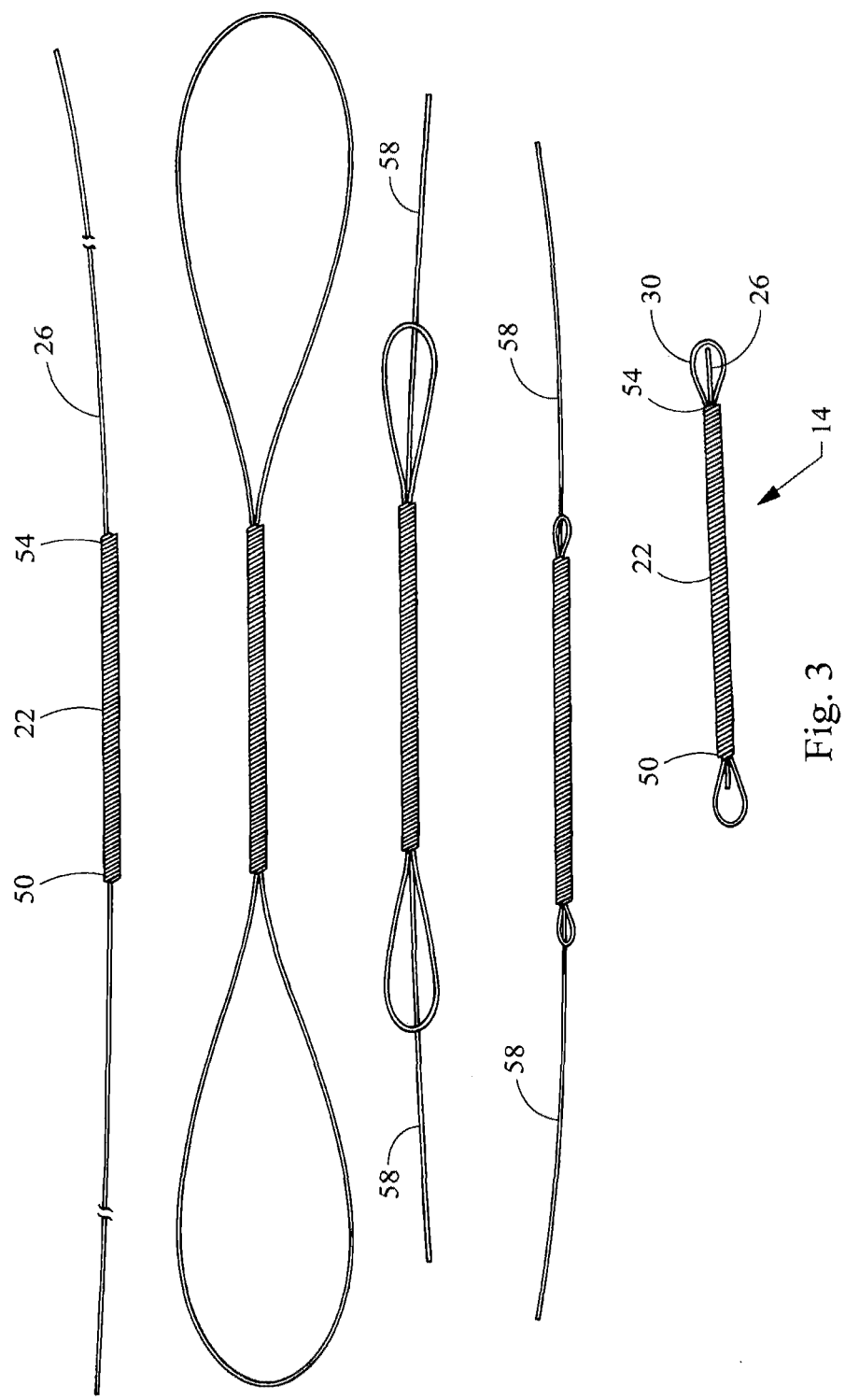
FIG. 3 shows a method for forming an anchor structure according to an aspect of the present invention.

In a preferred embodiment, terminally disposed loop structures 30 are formed from an anchor wire 26 extending through an anchor coil 22 proximal to each anchor coil end 50, 54, whereby one or both of the terminally disposed loops 30 are frictionally engaged by one or more of the anchor coils 22. FIG. 3 depicts a process for forming an anchor 14 containing terminally disposed loop structures 30 proximal to each anchor coil end 50, 54 in which an anchor wire 26 is passed through an anchor coil 22 three times. The loops 30 may be formed by extending an anchor wire 26 through the anchor coil 22, looping the anchor wire 26 back towards each open anchor coil end 50, 54, pulling the anchor wire 26 at each anchor coil end 50, 54 back through the anchor coil 22 in the opposite direction to achieve a desired loop size, and cutting off the excess anchor wire free ends 58 extending from each anchor coil end 50, 54. The free ends 58 may be looped back, knotted or crimped near the anchor coil ends 50, 54 to stabilize the terminally disposed loop structures 30 proximal to each anchor coil end 50, 54. By configuring the loop structures 30 to be wider than the anchor coil 22 diameter at each anchor coil end 50, 54, the grasping members or loop structures 30 are frictionally engaged by (or secured) by the anchor coil 22. Accordingly, grasping member(s) 30 may comprise structure(s) separate from that of an anchor coil 22 (or other hollow tubular variant thereof).

A closure device 10 of the present invention is made of flexible materials such that the closure device is sufficiently collapsible so as to facilitate retention and delivery from a variety of catheter delivery sizes, including 6-10 French size, preferably 6-8 French size. Accordingly, one or more of the component device parts of the closure device 10 may be made from flexible materials or shape memory alloy materials, such as Nitinol, including those described in U.S. Pat. Nos. 4,665, 906, 5,108,420.

Shape-memory materials may be included in a number of component device 10 parts, including, but not limited to the proximal and distal anchors 14, 16, the anchor coils 22, occluding body coils 34, grasping member(s) 30, anchor wires 26, and the occluding body wires 42. The shape-memory materials, including Nitinol alloys, may be utilized whereby the alloy material(s) is compressed or partially expanded in its martensitic state and fully expanded in its austenitic state. A specific shape memory alloy may be chosen so that the component device part is in the austenitic state at body temperature. Prior to insertion into the body, the device 10 or any of its component parts may be maintained at a low temperature within the martensitic range. Upon delivery to a desired bodily passageway, the device 10 may be warmed to at least the $A_f$ temperature so that it can expand to a desired, predetermined configuration.

Suitable shape-memory materials and their use in medical applications is disclosed in U.S. Pat. No. 3,012,882 to Muldawer et al.; U.S. Pat. No. 3,174,851 to Buechler et al.; U.S. Pat. No. 4,665,906 to Jervis; U.S. Pat. No. 5,108,420 to Marks; U.S. Pat. No. 5,769,796 to Palermo et al., U.S. Pat. No. 5,846,247 to Unsworth et al.; and U.S. Pat. No. 6,451,052 to Burmeister et al., the disclosures of which are expressly incorporated herein by reference.

Preferably, the anchor wires 26 and the occluding body wires 42 are made from or include shape memory alloy material(s). In a preferred embodiment, the anchor wires 26 and the occluding body wires 42 are made of Nitinol.

Sutures for linking elements of the closure device 10 to one another may be made from a variety of suture types, including braided or monofilament. Sutures may be made from polyester, polypropylene, polyglycolic acid, polytetrafluoroethylene (PTFE), SIS, nylon, silk or any of a variety of absorbable or nonabsorable suture materials known in the art. The sutures may be treated or coated with radiopaque materials to facilitate visualization of the device by radiography or fluoroscopy. The sutures may also be coated with antibiotics or other antimicrobial agents. Exemplary suture materials include TEVDEK II®, a braided polyester suture material impregnated with PTFE; DEKLENE II®, a polypropylene monofilament suture material, and nylon monofilament suture material, all of which are manufactured by Genzyme Biosurgery of Cambridge, Mass. Preferred suture materials include non-absorbable polypropylene sutures, such as PROLENE™ 6-0 mil (0.1524 mm) diameter (Ethicon Inc., Piscataway, N.J.).

Tissue adhesives may also be used for linking portions of the occluding body 18 to the anchors 14, 16. An exemplary tissue adhesive is BioGlue® (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) Am. Fam. Physician 61:1383-1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); and Bioglass (U.S. Biomaterials, Alachua, Fla.); CoStasis (Cohesion Technologies). MedPro Month (1999) 9:261-262; and MedPro Month (2000)10:86-91.

Bioremodelable Occluding Body Materials

In one aspect, the closure device includes a plug or tube of bioremodelable material suitably shaped to substantially fill the lumenal passageway of a bodily passageway. The bioremodelable material is designed to promote angiogenesis and endothelialization of the implanted closure device. In particular, the bioremodelable material is capable of remodeling the surrounding tissues, such that upon implantation in a patient, the bioremodelable material disposed in the lumenal passageway is degraded and replaced by the patient's endogenous tissues. As the bioremodelable material is remodeled by host tissues, the bodily passageway becomes stably closed, obviating concerns about migration of the device or leakage through the passageway.

The plug or tube of bioremodelable material may include or be made from reconstituted or naturally-derived collagenous materials. Suitable bioremodelable materials include collagenous ECM materials possessing biotropic properties, including in certain forms angiogenic collagenous extracellular matrix materials. Preferred ECMs include naturally-derived collagenous tissue materials retaining native matrix configurations and bioactive agents, such as growth factors, which serve to facilitate tissue remodeling, as opposed to collagen-based materials formed by separately purifying natural collagen and other associated components away from their native three dimensional matrix configurations or bioactive agents, including growth factors. Suitable collagenous ECMs include those derived from a variety of native tissues, including but not limited to, intestine, stomach, bladder, liver, fascia, skin, artery, vein, pericardium, pleura, heart valve, dura mater, ligament, tendon, bone, cartilage, bladder, liver, including submucosal tissues therefrom, renal capsule membrane, dermal collagen, serosa, mesenterium, peritoneum, mesothelium, various tissue membranes and basement membrane layers, including liver basement membrane, and the like. Suitable submucosa materials for these purposes include, for instance, intestinal submucosa, including small intestinal submucosa, stomach submucosa, urinary bladder submucosa, and uterine submucosa. A particularly preferred ECM material is porcine SIS material. Commercially available ECM materials capable of remodeling to the qualities of its host when implanted in human soft tissues include porcine SIS material (Surgisis® and Oasis® lines of SIS materials, Cook Biotech Inc., West Lafayette, Ind.) and bovine pericardium (Peri-Strips®, Synovis Surgical Innovations, St. Paul, Minn.).

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), platelet derived growth factor (PDGF), and other growth factors known to those of skill in the art. As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression, and combinations thereof.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon, or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example, at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material (C. Heeschen et al., Nature Medicine 7 (2001), No. 7, 833-839). When combined with a fluorescence microangiography technique, this model can provide both quantitative and qualitative measures of angiogenesis into biomaterials (C. Johnson et al., Circulation Research 94 (2004), No. 2, 262-268).

In addition to, or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (for example, human proteins applied to collagenous ECMs from other animals, such as pigs). The non-native bioactive components may also be drug substances Illustrative drug substances that may be incorporated into or onto the ECM materials used in the invention include, for example, antibiotics or thrombus-promoting substances such as blood clotting factors, for example, thrombin, fibrinogen, and the like. These substances may be applied to the ECM material as a premanufactured step, immediately prior to the procedure (for example, by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al., which is incorporated by reference herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

A preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants and better preserves the aseptic state and inherent biochemical form of the submucosa, thereby potentiating its beneficial effects. Alternatively, the ECM- or submucosa may be purified a process in which the sterilization step is carried out after delaminabon as described in U.S. Pat. Nos. 5,993,844 and 6,572,650.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example, by chemical treatment, the matrix structure may be wrapped in a plastic or foil wrap and sterilized again using electron beam or gamma irradiation sterilization techniques.

Bioremodelable materials, including ECMs according to the present invention, may be isolated and used in the form of intact natural sheets, tissue layers, or strips, which may be optimally configured from a native, wet, dry, fluidized, foam formulations or states, into sheets, knitted meshes, or porous scaffolds, using one or more of the following, including stretching, chemical crosslinking, lamination under dehydrating conditions, compression under dehydrating conditions, in accordance with teachings set forth in U.S. Pat. Nos. 6,206,931 and 6,358,284; U.S. Patent Application Publication Nos. 2006/0201996, 2006/0052816, 2005/0249772, 2004/10166169, and 2003/0021827, the disclosures of which are expressly incorporated by reference herein.

In addition, bioremodelable materials according to the present invention may be treated by controlled autolysis to render the materials substantially acellular and less susceptible to post-implantation mineralization as described in U.S. Pat. Nos. 5,595,571, 5,720,777, 5,843,180, and 5,843,181, the disclosures of which are expressly incorporated by reference herein.

Other Biocompatible Occluding Body Materials

Bioremodelable materials provide a preferred source of biocompatible materials for the plug or tube. However, other biocompatible materials may be used in place of bioremodelable materials. These other biocompatible occluding body materials include virtually any natural or synthetic polymeric material known to those of skill in the art which can be formed into a plug or tube. Exemplary biocompatible occluding body materials include polymeric materials; fibrous materials; thrombogenic fibrous materials; expandable matrix materials; hydrogels, and other materials known to those of skill in the art as expanding upon contact with liquids or bodily fluids.

Occluding body materials may be formed from fibers, or any suitable material (natural, synthetic, or combination thereof) that is pliable, strong, resilient, elastic, and flexible. The material should be biocompatible or capable of being rendered biocompatible by coating, chemical treatment, or the like. Thus, in general, the material may comprise a synthetic biocompatible material that may include, for example, bioresorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof; polyurethanes, including THORALON™ (THORATEC, Pleasanton, Calif.), as described in U.S. Pat. Nos. 4,675,361, 6,939,377, and U.S. Patent Application Publication No. 2006/0052816, the disclosures of which are incorporated by reference herein; cellulose acetate, cellulose nitrate, silicone, polyethylene terephthalate, polyamide, polyester, polyorthoester, polyanhydride, polyether sulfone, polycarbonate, polypropylene, high molecular weight polyethylene, polytetrafluoroethylene, or mixtures or copolymers thereof, a polyanhydride, polycaprolactone, polyhydroxy-butyrate valerate, polyhydroxyalkanoate, or another polymer able to be made biocompatible.

Thrombogenic fibrous materials include synthetic and/or natural fibrous material having thrombogenic properties. Exemplary thrombogenic fibrous materials include, but are not limited to, DACRON, cotton, silk, wool, polyester thread and the like.

The polymeric materials may include a textile material. The textile includes fibers and may take many forms, including woven (including knitted) and non-woven. Preferably, the fibers of the textile comprise a synthetic polymer. Preferred textiles include those formed from polyethylene terephthalate, polytetrafluoroethylene (PTFE), and expanded polytetrafluoroethylene (ePTFE). These materials are inexpensive, easy to handle, have good physical characteristics and are suitable for clinical application. These materials may be attached to or rolled around a hollow tube or coil as described above.

Examples of biocompatible materials from which textiles can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile material, provided the final textile is biocompatible. Polymeric materials that can be formed into fibers suitable for making textiles include polyethylene, polypropylene, polyaramids, polyacrylonitrile, nylons and cellulose, in addition to polyesters, fluorinated polymers, and polyurethanes as listed above. Preferably the textile is made of one or more polymers that do not require treatment or modification to be biocompatible. More preferably, the textile is made of a biocompatible polyester. Examples of biocompatible polyesters include DACRON (DUPONT, Wilmington, Del.) and TWILLWEAVE MICREL (VASCUTEK, Renfrewshire, Scotland).

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver, disclosure of which is incorporated by reference. Fibers similar to those described are currently being manufactured by the DuPont Company from polyethylene terephthalate (often known as "DACRON" when manufactured by DuPont), and by other companies from various substances.

Expandable matrix materials may include at least one water permeable polymeric material in combination with one or more osmotically active agents. Exemplary water permeable polymeric materials include silicone. Other biocompatible elastomeric polymers include polyvinyl alcohol or poly (ethylene oxide), or polyurethane. The expandable matrix may include one or more osmotically active agents such as, glycerol, sodium chloride, or calcium chloride. Other equivalent agents can also be useful for forming the expandable matrix include mannitol, glucose, dextran, potassium chloride, sodium phosphate, or any other non-toxic water soluble material that does not adversely affect curing of the water permeable polymer.

Expandable matrix materials may be adapted to absorb water upon contact with a fluid environment. As water is absorbed, the matrix begins to swell in physical size and continues to swell until, in one embodiment, the osmotically active agent is consumed. Alternatively, in another embodiment, the expandable matrix swells until the internal pressure of the matrix is matched by a source of external pressure of, for example, the polymer or structure surrounding the polymer. The rate of expansion and/or the amount of expansion can be controlled by the selection of the polymer, the additive, and the particle size of the additive.

Examples of suitable bioresorbable materials that expand when contacted by water include hydrogels, collagen, polysalactic acid, and any other suitable hydrophilic agents. Examples of polymers that swell in the presence of aqueous fluids such as biological fluids, include the following polymers, most of which are hydrogels. Synthetic hydrogels can be prepared from the following classes of polymers and these are generally considered to be non-biodegradable:poly (hydroxyalkyl methylacrylates) such as poly(glyceryl methacrylate)poly(acrylamide) and poly(methacrylamide) and derivatives; poly(N-vinyl-2-pyrrolidone)anionic and cationic hydrogels; poly(vinyl alcohol)poly(ethylene glycol) diacrylate and derivatives from block copolymers composed of poly(ethylene oxide)-poly(propylene oxide)-poly(ethylene oxide) and poly(propylene oxide)-poly(ethylene oxide)-poly (propylene oxide) blocks, respectively; All of the above can be cross-linked with agents such as ethylene glycol dimethacrylate or methylene-bis-acrylamide.

Biodegradable synthetic hydrogels (as listed above) can be prepared from the above polymers by incorporating one or more monomers, such as Glycolide, Lactide, e-Caprolactone, p-Dioxanone and Trimethylene Carbonate. In addition, biodegradable hydrogels can be based on natural products including polypeptides such gelatin which may be cross-linked with formaldehyde or glutaraldehyde and various other dialdehydes.

Expandable plug or tube materials, hydrogel materials, foam materials, and methods for molding or machining such materials into a plug or tube are further described in U.S. Patent Application Numbers 2006/0008419, 2005/0085885, and 2003/0109899, the disclosures of which are incorporated by reference herein.

Non-native bioactive components, such as those synthetically produced by recombinant technology or other methods, may be incorporated into these other biocompatible materials. These non-native bioactive components may be naturally-derived or recombinantly produced proteins, such as growth factors, which are normally found in ECM tissues. These proteins may be obtained from or engineered from any animal species. The non-native bioactive components may also be drug substances. Illustrative drug substances that may be incorporated into or onto the ECM materials used in the invention include, for example, antibiotics or thrombus-promoting substances such as blood clotting factors, for example, thrombin, fibrinogen, and the like. These substances may be applied to the biocompatible material as a premanufactured step, immediately prior to the procedure (for example, by soaking the material in a solution containing a suitable antibiotic such as cefazolin), or during or after engraftment of the material in the patient.

Closure Device Assembly

Figure 4A:
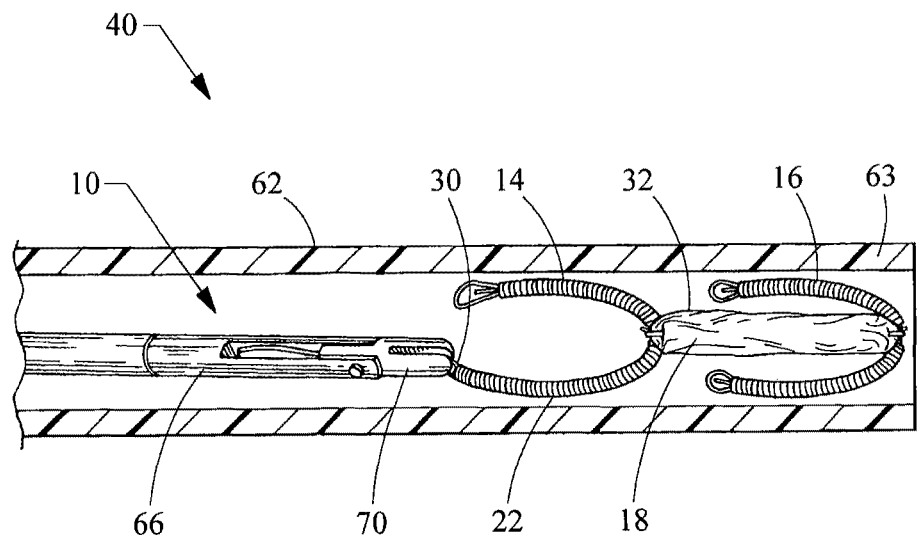
FIG. 4A shows a closure device assembly according to an embodiment of the present invention.

In a further aspect, an assembly 40 for delivering a closure device 10 according to the present invention is provided. In FIG. 4A, the closure device assembly 40 includes a delivery catheter 62, an anchor engaging member 66, and a collapsibly disposed closure device 10. Any of the above-described closure devices 10 may be used. In general, the closure device 10 includes an occluding body 18 connected between a proximal anchor 14 and a distal anchor 16, the occluding body 18 containing a plug or tube 32 of bioremodelable material configured to occlude a bodily passageway.

Each of the anchors 14, 16 comprises a flexible, substantially one-dimensional linear structure. The anchor engaging member 66 is linked to at least one of the two anchors 14, 16 by way of one or more grasping member(s) 30. The anchor engaging member 66 facilitates release of the closure device 10 during the process of deployment.

The anchor engaging member 66 includes an anchor engagement portion 70 releasably attached to one or more grasping member(s) 30. The anchor engagement portion 70 may be linked to one or more grasping members 30 in the proximal anchor 14. In a preferred embodiment, the anchor engaging member 66 comprises biopsy forceps containing anchor engagement portions in the form of cups or jaws 70. Suitable biopsy forceps for use in the present invention include Cup Biopsy Forceps (Cook Urological, Inc., Spencer, Ind.) and Biopsy Cup Forceps (ACMI Corp., Southborough, Mass.).

In FIG. 4A, the grasping member is depicted as a single loop 30 connected to a biopsy forceps 66 by way of an anchor engagement portion 70 depicted as a pair of cups. The anchor engagement portion 70 may include a ball, hook, loop, a pair of cups or jaws, or any other configuration suitable for releasable attachment to one or more grasping member(s) 30.

The delivery catheter 62 may be configured for "long wire" or "over-the-wire" (OTW) delivery or for "short wire" or rapid exchange (RE) delivery procedures known to those of skill in the art. Accordingly, the delivery catheter 62 may be structurally modified with apertures or structural components allowing exchange from, for example, a multi-purpose catheter to the delivery catheter 62 by RE without the need to replace the wire guide with an exchange-length guide wire before exchanging the catheters. Exemplary RE catheters that may be used to deliver the closure device 10 of the present invention are described in U.S. Pat. Nos. 5,690,642; 5,814,061; 6,371,961; and U.S. Pat. Application Nos. 2005/0070794; 2005/0125050; and 2005/0070821, the disclosures of which are expressly incorporated by reference herein.

Figure 4B:
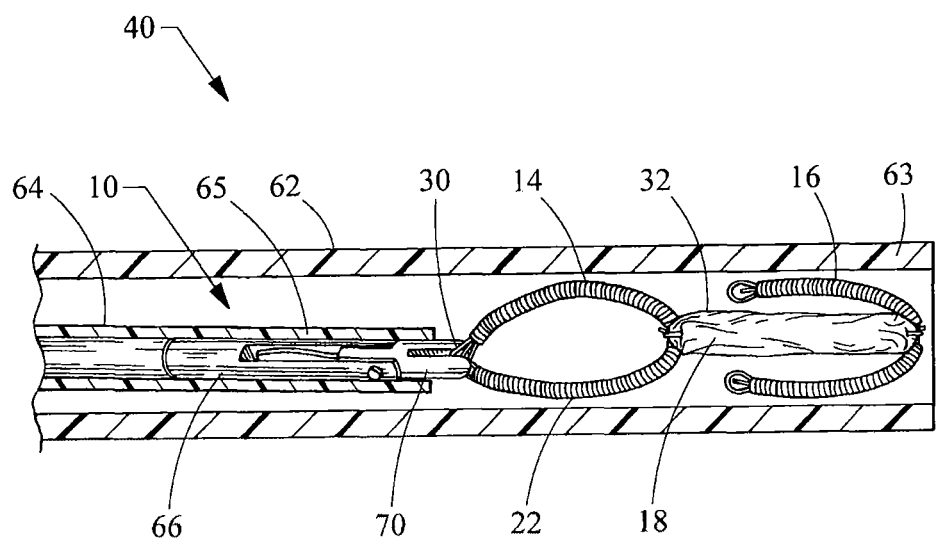
FIG. 4B shows a closure device assembly according to another embodiment of the present invention.

FIG. 4B depicts an anchor engaging member 66 positioned in a locking catheter 64, which provides an additional safety feature preventing premature disengagement of the closure device 10 from the anchor(s) 14, 16 prior to or during release of some or all of the device 10 from the delivery catheter 62. In particular, the delivery catheter 62 further includes a biopsy forceps 66 which is passed through a smaller, coaxially positioned locking catheter 64. In FIG. 4B, the biopsy cups 70 of the biopsy forceps 66 are connected to two terminally disposed loop structures 30a, 30b in the proximal anchor 14. The locking catheter 64 and the biopsy forceps 66 are configured so that the biopsy cups (or jaws) 70 are prevented from inadvertently releasing the closure device 10 while positioned inside the delivery catheter 62. In particular, the distal end of the locking catheter sheath 65 overhangs at least a portion of the biopsy cups (or jaws) 70, thereby preventing premature disengagement of the proximal anchor 14 from the biopsy forceps 58 prior to or during release of some or all of the device 10 from the delivery catheter 62.

In a preferred embodiment, the closure device assembly 40 includes a delivery catheter 62 with a curved flexor catheter sheath, and a collapsibly disposed closure device 10 preloaded near the tip of the delivery catheter 62, which is connected to a biopsy forceps 66 held within a locking catheter 64. In a particularly preferred embodiment, the closure device assembly 40 includes a curved 6, 7, or 8 French delivery catheter 62; a 4 or 5 French locking catheter 60 housing the biopsy forceps 66; and a collapsibly disposed closure device 10. Flexor® Introducer Sets (Cook Medical Inc., Bloomington, Ind.) provide a preferred source of delivery catheters for use in the present invention.

The closure device 10 is made from sufficiently flexible materials to enable the device 10 to be collapsibly disposed within a relatively small delivery catheter 62 (including 6 to 8 French). The closure device may be preloaded at the tip of the delivery catheter 62 in an unexpanded, first configuration. When the closure device 10 is expelled from the delivery catheter 62, it may expand to a second, expanded configuration, particularly when the closure device 10 is made from shape memory materials. Non shape memory materials, such as stainless steel and the like, may be used for closure devices 10 requiring a lower degree of compression or expansion upon release.

Additionally, FIGS. 4 and 5 depict the proximal 14 and distal 16 anchors as being collapsibly disposed in the delivery catheter 62 whereby the anchors 14, 16 are in a substantially parallel configuration, such that the anchors 14, 16 are folded in an inward direction away from the distal tip. Alternatively, the distal anchor 16 may be collapsibly disposed in an outwardly folded configuration so that the anchor ends or grasping members 30 are facing toward the distal tip of the delivery catheter 62.

To enhance the shelf life of the closure device containing bioremodelable materials, the device 10 may be lyophilized in an elongated form inside a cartridge sheath having a similar inner diameter (I.D.) sheath size as the delivery catheter 62 (for example, 6-8 French size). In view of their low device profile, it is believed that closure devices 10 of the present invention can be delivered and securely deployed from a single, tip preloaded delivery catheter 62 for immediate, substantial or complete passageway closure in as little as 15 minutes.

In a preferred embodiment, the closure device assembly 40 includes a delivery catheter 62 with a curved sheath 63, and a collapsibly disposed closure device 10 preloaded near the tip of the delivery catheter 62, whereby the closure device 10 is connected to a biopsy forceps 66 held within a locking catheter 64. In a particularly preferred embodiment, the closure device assembly 40 includes a curved 6, 7, or 8 French delivery catheter 62 (having an I.D. of 0.087 inches, 0.100 inches, or 0.113 inches, for example); a 5 French locking catheter 64 (having an I.D. of 0.074 inch I.D.) holding the biopsy forceps 66; and a collapsibly disposed closure device 10. Flexor® Introducer Sets (Cook Medical Inc., Bloomington, Ind.) provide a preferred source of delivery catheters for use in the present invention.

Method For Closing A Bodily Passageway

In a further aspect, the present invention provides a method for closing or occluding a bodily opening in a patient using a closure device 10 or closure device assembly 40 as described above. In a preferred embodiment, a method for closing or occluding a septal opening, such as a PFO, using the above described closure device assembly is provided.

By way of example, FIGS. 5A-5D depict a method for closing a PFO with a closure device assembly 40 according to the present invention. In this example, multiple delivery components are included in the closure device assembly 40 to allow completion of the deployment process in as little as 10-15 minutes The closure device assembly 40 includes a delivery catheter 62, a closure device 10 collapsibly disposed therein, and an anchor engaging member 66 (herein depicted as biopsy forceps) to facilitate closure device 10 delivery.

Figure 5A:
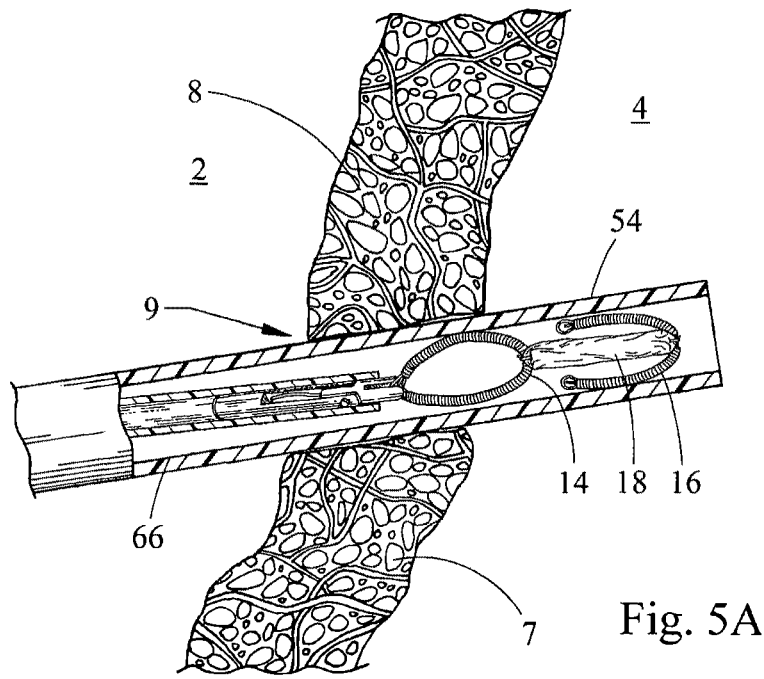
FIG. 5A shows a cross-sectional view of the distal end of the closure device assembly of FIG. 4B inserted and extending through a PFO.

The closure device 10 includes a proximal anchor 14 and a distal anchor 16 linked to an occluding body 18. In FIG. 5A, each of the proximal and distal anchors, 14, 16 includes an anchor coil 22 with one or more anchor wires 26 extending longitudinally therethrough. The proximal anchor 14 includes two terminally disposed grasping members 30 (herein depicted as wire loop structures) for releasable attachment to the anchor engagement portion 70 (herein depicted as cups or jaws) of the biopsy forceps 66. To prevent inadvertent release of the closure device 10 from the anchor engaging member 66 when held in a compressed state inside the delivery catheter 62, the anchor engaging member 66 is preferably positioned in a locking catheter 64.

Figure 5B:
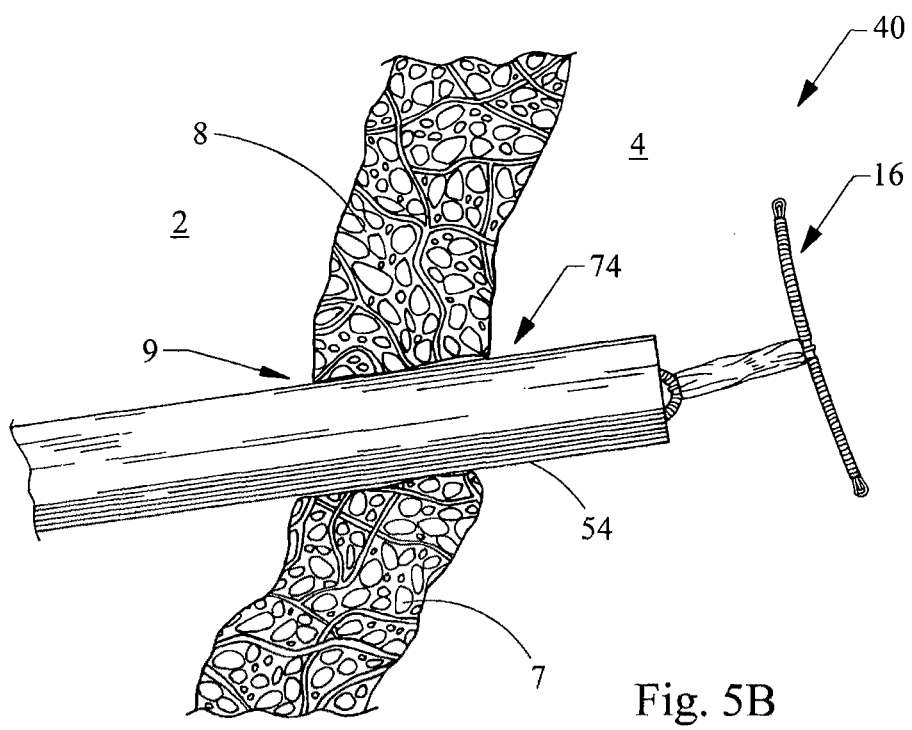
FIG. 5B shows a cross-sectional view of the distal end of the closure device assembly of FIG. 4B extending through a PFO and releasing a distal anchor proximal to the distal side of the PFO opening.

An exemplary method for delivering any one of the above-described closure devices 10 includes passing a stiff guide wire through a suitable multi-purpose catheter and positioning the guide wire in the left atrium 4 across a bodily passageway, such as a PFO. In FIG. 5A, the delivery catheter 62 of the closure device assembly 40 is introduced over the wire guide 68 and is positioned into the left atrium 4 of a patient, through the PFO 9 (FIG. 5A). Before releasing the device 10 or any part thereof, its position may be assessed by contrast media injection the delivery catheter 62. Following confirmation of left atrium 4 positioning, the distal anchor 16 is released into the left atrium 4 proximate to the distal opening 74 of the PFO (FIG. 5B). This may be performed by retracting the delivery catheter sheath 63.

To prevent inadvertent release of the closure device 10 when held in a compressed state inside the delivery catheter 62, the anchor engaging member 66 (depicted here as biopsy forceps) may be positioned in a locking catheter 64. Once the sheath 65 of the locking catheter 62 is pulled back, the tips (or jaws) 70 of the biopsy forceps 66 can be released from the grasping member(s) 30 (depicted here as terminally disposed loop structures) in the proximal anchor 14. In addition, the locking catheter may be used as a pusher to release the distal anchor 16 and occluding body 18.

Following the release of the distal anchor 16, the occluding body 18 is released from the delivery catheter 62 while the catheter 62 retracted through the PFO 9. The occluding body 18 may be released by retracting the sheath of the delivery catheter 62 or by advancing the locking catheter 64 toward the distal catheter end. At this point, the proximal anchor 14 is pulled against the septum primum 7 and the septum secundum 8 and positioned toward the distal end of the delivery catheter 62 in the right atrium near the proximal opening 78 of the PFO passageway (FIG. 5C). Following proper confirmation of right atrium 2 device 10 positioning, the locking catheter sheath 65 may be pulled back to disengage the biopsy cups 70 from the proximal anchor 14, thereby releasing the proximal anchor 14 into the right atrium 2 near the proximal opening 78 of the PFO 9 (FIG. 5D). Alternatively, the biopsy cups 70 can become disengaged by advancing biopsy forceps 66 out of the locking catheter sheath 65. Upon release from the delivery catheter 62, the proximal and distal anchors 14, 16 linearly expand and spring back against the septum primum 7 and septum secundum 8, anchoring the occluding body 18 and occluding device 10 through the PFO 9 (FIG. 5E). The delivery catheter 62, locking catheter 64, and biopsy forceps 66 are then retracted and removed.

The closure device 10 is self-expanding and retains its original shape following release. Thus, the anchors 14, 16 linearly expand and the occluding body 18 radially expands to stably occlude at least a portion of the PFO passageway 9. Preferably, the occluding body 18 includes ECM or submucosal tissue material configured to stimulate angiogenesis and to expand upon its release into the bodily passageway so as to occlude at least a portion of the bodily passageway and have at least a portion of the ECM or submucosal tissue stably absorbed and replaced by host tissues.

As an alternative to the pre-assembled over-the-wire assembly described above, one can alternatively introduce and position a wire guide through a suitable catheter or sheath near the site of the passageway opening; load the collapsible closure device 10 into the sheath; push the closure device 10 to the desired site with a biopsy forceps, pushing catheter or other suitable pushing device; and release the closure device 10 as described above.

Visualization of the assembly 40 within the interior of the heart during deployment may be provided by various means. For example, fluoro-visible or radio-opaque dyes may be injected into the cardiac chambers and venous anatomy so that the chambers of the heart and the related vasculature are visible using a fluoroscopic device. This procedure, sometimes referred to as a venogram, allows the surgeon to locate a precise site and achieve proper device placement when performing an implant procedure.

Additionally, an ultrasonic probe may be positioned in the patient's esophagus, on the surface of the patient's chest, or in the chest cavity adjacent or in contact with the exterior of the heart to ultrasonically image the interior of the heart. In particular an intravascular ultrasound (IVUS) catheter may be utilized in conjunction with the above assembly 40 to provide ultrasonic imaging. Alternatively, an endoscope with a translucent bulb or balloon over its distal end may be introduced into the heart through the closure device assembly or through a separate incision in the wall of the heart to allow video-based or direct visualization of the interior of the heart. An angioscope introduced into the heart endovascularly through a peripheral vessel may also be used for intracardiac visualization. Fluoroscopy or magnetic resonance imaging (MRI) may provide an additional means for visualization.

Sheaths, dilators, catheters, guide catheters, pushing catheters, wire guides, and needles used in the present invention can all be conventional marketed products or modifications thereof. For example, sheaths can be formed from PTFE (for example, Teflon) or polyamide (for example, Nylon) material, or a combination of materials such as an assembly including an inner layer of PTFE, a flat wire coil over the PTFE for kink resistance, and a polyamide (Nylon) outer layer to provide integrity to the overall structure and a smooth surface (as in the Flexor® Introducer Sets, Cook Medical Inc., Bloomington, Ind.). Dilators can be made from conventional dilator/catheter type materials such as polyethylene, polyamide, polyurethane or vinyl, or any combination of these materials. Fittings provided for sheath/dilator assemblies can be conventional elements such as luer locks; the dilator and the locking catheter can have fittings allowing them to be locked to the sheath during insertion and manipulation. Catheters can be made from conventional materials such as polyethylene, polyamide, PTFE, polyurethane, and other materials. Assembly components, including biopsy forceps may be separately housed in coaxially positioned interlumenal sheaths within the delivery catheter or they may be disposed through secondary lumenal portions formed in the delivery catheter, as in double lumen catheters and the like.

The delivery catheter 62 includes a sheath 63 having a lumen diameter sized to allow for the introduction of the closure device to occlude the bodily passageway of interest. Illustratively, the inner diameter (I.D.) of the delivery sheath may range from about 6 to 10 French or more, depending on the size of the closure device and the bodily passageway for closure. In preferred embodiments the delivery catheter includes an inner diameter of 6-8 French.

Radiopaque marker materials may be added to one or more components of the closure device 10 or assembly 40 so as to render them radiopaque or MRI compatible. In particular, radiopaque materials, fillers, metallic marker bands or powders may be included into one or more of the proximal and distal anchors 14, 16, anchor coils 22, anchor wire 26, grasping member 30, occluding body coil 34, occluding body wires 42, delivery catheter 62, or component parts thereof, to facilitate radiographic visualization of the device during the implantation process.

Exemplary radiopaque marker materials include but are not limited to, platinum, gold, tungsten, tantalum, tantalum powder, bismuth, bismuth oxychloride, barium, barium sulphate, iodine and the like. Metallic bands of stainless steel, tantalum, platinum, gold, or other suitable materials, can include a dimple pattern, which can further facilitate ultrasound or X-ray identification.

Radiopaque markers may be introduced in any form suitable for the rendering the closure device radiopaque or MRI compatible. In addition, the radiopaque materials can be incorporated in the closure device or assembly components by a variety of common methods, such as adhesive bonding, lamination between two material layers, vapor deposition, and the materials and methods described in U.S. 2003/0206860, the disclosure of which is incorporated herein by reference.

A closure device 10 or assembly 40 according to the present invention is particularly suited for closing septal heart defects, including PFOs and other atrial septal or ventricular septal defects. However, the closure device 10 can be similarly applied to closing or occluding a variety of other heart openings, tissue openings, vessels, vessel punctures, ducts, and other tissue openings where closure is desired.

Closure Device Repositioning or Removal

In some instances it may be necessary to reposition or remove the closure device, particularly when it includes sufficiently flexible materials or a sufficiently flexible structural configuration. This may occur where the device is not appropriately positioned or sized for a particular bodily passageway and/or fails to completely seal the passageway. In cases where it is necessary or advisable to reposition the closure device prior to full deployment, an anchor engaging member, including biopsy forceps, may be used to reposition the device. In this case, the anchor engaging member or biopsy forceps still connectively linked to the proximal anchor may be pushed back into the side of the bodily passageway holding the distal anchor, whereby the device can be pulled back into the delivery sheath, at which point repositioning of the device can be re-initiated prior to full deployment (and release) of the proximal anchor In cases where it is necessary or advisable to remove the closure device, a suitable foreign body retrieval device, such as a snare, may be used to remove the device. The snare may be delivered through the introducer sheath using a snare catheter. Preferred snares are commercially available under the trade names Needle's Eye® Snare (Cook Medical, Bloomington, Ind.) and Microvena Amplatz Goose Neck® Snare (ev3 Inc., Plymouth, Minn.). After positioning the snare around the proximal anchor and advancing the anchor through the passageway where the distal anchor is held, the device can be pulled back into a delivery catheter sheath and removed.

EXAMPLES

Use of an H-Shaped Closure Device to Close a Bodily Passageway in an Animal.

To demonstrate the ability of an H-shaped closure device to close a bodily passageway, an experiment was conducted in a swine having a 5 mm diameter PFO. As evidenced by contrast injection, deployment of the device through the PFO produced immediate closure.

It is intended that the foregoing detailed description be regarded as illustrative rather than limiting, and that it be understood that it is the following claims, including all equivalents, that are intended to define the spirit and scope of this invention.

The invention claimed is:

1. A closure device for occluding a bodily passageway comprising:
an occluding body connectively linked between proximal and distal anchors, the occluding body comprising a plug or tube of biocompatible material having a hole longitudinally disposed therethrough, the occluding body configured to occlude the passageway; and
a body tube or body coil extending through the hole,
wherein the proximal anchor comprises a first hollow tube or first hollow coil having a first anchor wire extending longitudinally therethrough, the first anchor wire comprising at least one terminally disposed grasping member, wherein the first anchor wire passes through the first hollow coil or first hollow tube at least two times,
wherein the distal anchor comprises a second hollow tube or second hollow coil having a second anchor wire extending longitudinally therethrough,
wherein each of the proximal and distal anchors is a flexible structure configured to anchor the occluding body in a bodily passageway so as to occlude the passageway.

2. The device of claim 1, wherein the at least one terminally disposed grasping member of the first anchor wire is in the form of a terminally disposed loop structure frictionally engaged by the first hollow tube or first hollow coil, wherein the second anchor wire comprises at least one grasping member in the form of a terminally disposed loop structure frictionally engaged by a second hollow tube or second hollow coil.

3. The device of claim 1, wherein at least one wire extends through the body tube or body coil, the at least one wire connectively linking and directly attaching the occluding body to the proximal and distal anchors.

4. The device of claim 1, wherein the occluding body is adapted to expand radially in a deployed state,
wherein at least one wire extends through the body tube or body coil, the at least one wire connectively linking the occluding body to the proximal and distal anchors.

5. The device of claim 1, wherein the at least one terminally disposed grasping member comprises a loop, wherein the first anchor wire and the loop have a one-piece construction.

6. The device of claim 1, wherein each of the proximal and distal anchors extend along respective lines that are perpendicular to a longitudinal length of the occluding body.

7. The device of claim 1, wherein the second anchor wire passes through the second hollow coil or second hollow tube at least two times.

8. The device of claim 1, wherein the first anchor wire passes through the first hollow coil or first hollow tube three times, wherein the second anchor wire passes through the second hollow coil or second hollow tube three times.

9. A closure device for occluding a bodily passageway comprising:
an occluding body positioned between proximal and distal anchors, the occluding body comprising a plug or tube of biocompatible material having a hole longitudinally disposed therethrough, the occluding body configured to occlude a bodily passageway;
a hollow occluding body tube or occluding body coil extending through the hole;
at least one wire extending through the hollow occluding body tube or hollow occluding body coil, the at least one wire connectively linking the occluding body to the proximal and distal anchors;
wherein at least the proximal anchor comprises at least one grasping member, and
wherein each of the proximal and distal anchors is a flexible structure configured to anchor the occluding body in a bodily passageway so as to occlude the passageway,
wherein the proximal anchor comprises a first hollow coil or first hollow tube having a first anchor wire extending therethrough, wherein the first anchor wire passes through the first hollow coil or first hollow tube at least two times,
wherein the distal anchor comprises a second hollow tube or second hollow coil having a second anchor wire extending longitudinally therethrough.

10. The device of claim 9, wherein the plug or tube of biocompatible material comprises bioremodelable tissue material.

11. The device of claim 9, wherein the plug or tube of biocompatible material comprises expandable submucosal tissue material.

12. The device of claim 9, wherein the plug or tube of biocompatible material comprises expandable hydrogel material.

13. The device of claim 9, wherein the occluding body is cylindrical about a length extending between the respective anchors, and is adapted to expand radially in a deployed state.

14. The device of claim 9, wherein in a deployed state each anchor comprises a linear structure extending along a line perpendicular to a longitudinal axis extending through a length of the occluding body, and wherein each anchor is capable of rotating relative to the longitudinal axis of the occluding body when deployed.

15. The device of claim 9, wherein the at least one grasping member is in the form of a terminally disposed loop structure that is integrally formed with the first anchor wire.

16. The device of claim 9, wherein the at least one grasping member is frictionally engaged by said first hollow tube or first hollow coil.

17. The device of claim 9, wherein the proximal anchor comprises the first hollow coil, wherein the distal anchor comprises the second hollow coil, the at least one grasping member comprising a first proximal terminally disposed loop, the proximal anchor comprising a second proximal terminally disposed loop, the distal anchor comprising first and second distal terminally disposed loops.

18. A closure device assembly comprising:
the closure device of claim 9 disposed in a delivery catheter comprising an anchor engaging member, wherein the anchor engaging member is connectively linked to the at least one grasping member.

19. The device assembly of claim 18, wherein the proximal anchor comprises the first hollow coil, wherein the distal anchor comprises the second hollow coil, the first hollow coil frictionally engaging the at least one grasping member linked to the anchor engaging member, the anchor engaging member comprising an anchor engagement portion comprising at least one structure selected from the group consisting of hook, ball, loop, cup, and jaw.

20. The device assembly of claim 18, wherein the delivery catheter further houses a locking catheter housing the anchor engaging member, the locking catheter being secured to the anchor engaging member so that the closure device is prevented from being released inside of the delivery catheter.

21. A method for occluding a bodily passageway in a patient comprising:
providing the closure device assembly of claim 18;
advancing the delivery catheter through the bodily passageway;
releasing the proximal anchor of the closure device from the catheter proximate to a first end of the bodily passageway;
positioning the delivery catheter proximate to a second end of the bodily passageway opposite to the first end; and
disengaging and releasing the distal anchor of the closure device from the anchor engaging member proximate to the second end,
wherein the proximal and distal anchors are secured to tissue portions surrounding the ends of the bodily passageway and the occluding body is disposed within the bodily passageway, thereby occluding the bodily passageway.

* * * * *